United States Patent [19]
Murthy et al.

[11] Patent Number: 5,962,689
[45] Date of Patent: Oct. 5, 1999

[54] STEREOSELECTIVE AND USEFUL PREPARATION OF 3-SUBSTITUTED 4-ARYL PIPERIDINE COMPOUNDS

[75] Inventors: K. S. Keshava Murthy; Allan W. Rey, both of Brantford, Canada

[73] Assignee: Brantford Chemicals Inc., Canada

[21] Appl. No.: 08/914,189

[22] Filed: Aug. 19, 1997

[30] Foreign Application Priority Data

Aug. 7, 1997 [CA] Canada ................................. 2212451

[51] Int. Cl.$^6$ ..................... C07D 211/02; C07D 405/12
[52] U.S. Cl. ........................... 546/185; 546/197; 546/236
[58] Field of Search ................................. 546/185, 197, 546/225, 236

[56] References Cited

U.S. PATENT DOCUMENTS

| | | | |
|---|---|---|---|
| 3,912,743 | 10/1975 | Christensen et al. | 260/293.58 |
| 4,007,196 | 2/1977 | Christensen et al. | 260/293.58 |
| 5,039,803 | 8/1991 | Smith et al. | 546/185 |

OTHER PUBLICATIONS

Engelstoft, M. et al.: Synthesis and 5–HT modulating activity of Stereoisomers of 3–Phenoxymethyl–4–Phenylpiperidines. *Acta Chem. Scand.* vol. 50, pp. 164–169, 1996.

Hassan, S.M. et al., "A comparison of the effect of paroxetine and amitriptyline on the tyramine pressor response test", *Brit. J. Clin. Pharmacol.*, (1985), vol. 19, pp. 705–706.

Dahl, L.E. et al., "Antidepressant effect of femoxetine and desipramine and relationship to the concentration of amine metabolites in cerebrospinal fluid", *Acta Psychiat. Scand.*, (1982), vol. 66, pp. 9–17.

Reebye, P.N. et al., "A Controlled Double–blind Study of Femoxetine and Amitriptyline in Patients with Endogenous Depression", *Pharmacopsychiat.*, (1982), vol. 15, pp. 164–169.

Amat, M., et al., "Synthesis of Enantiopure 3,4–Disubstituted Piperidines. An Asymmetric Synthesis of (+)–Paroxetine", *Tetrahedron: Asymmetry*, (1996), vol. 7, No. 6, pp. 1591–1594.

Rossiter, B.E. et al., "Asymmetric Conjugate Addition", *Chem. Rev.*, (1992), vol. 92, pp. 771–806.

Meth–Cohn, O., "Transesterification of Methyl Esters of Aromatic and α,β–Unsaturated Acids with Bulky Alcohols: (–)–Menthyl Cinnamate and (–)–Menthyl Nicotinate", *Organic Syntheses*, (1993), vol. VIII, pp. 350–353.

Ho, G–J, et al., "Lithium–Initiated Imide Formation. A Simple Method for N–Acylation of 2–Oxazolidinones and Bornane–2,10–Sultam", *J. Org. Chem.*, (1995), vol. 60, pp. 2271–2273.

Christensen, J.A., et al., "On the Formation of the 1–AZA–[3.1.1]–Bicycloheptane Ring System", *Tetrahedron Letters*, (1983), vol. 24, No. 46, pp. 5151–5152.

*Primary Examiner*—Alan L. Rotman
*Assistant Examiner*—Charanjit S Aulakh
*Attorney, Agent, or Firm*—Ivor M. Hughes; Neil H. Hughes; Marcelo K. Sarkis

[57] ABSTRACT

This invention relates to new stereoselective processes for preparing 3-substituted-4-aryl piperidines and methods for controlling the absolute stereochemistry at the C-3 and C-4 positions of the piperidine ring. Compounds of this type are key intermediates in the preparation of paroxetine, femoxetine, and other medicaments.

23 Claims, No Drawings

STEREOSELECTIVE AND USEFUL PREPARATION OF 3-SUBSTITUTED 4-ARYL PIPERIDINE COMPOUNDS

BACKGROUND OF THE INVENTION

Paroxetine (I) and femoxetine (II) are closely related serotonin (5-hydroxytryptamine) reuptake inhibitors which have been used clinically for the treatment of depression. (S. M. Hassan et al., Brit. J. Clin. Pharmacol., 19, 705, 1985; L. E. Dahl et al., Acta Psychiatr. Scand., 66, 9, 1982; P. N. Reebye et al., Pharmacopsychiatria, 15, 164, 1982). U.S. Pat. No. 3,912,743 delineates some of paroxetine's and femoxetine's pharmacological properties.

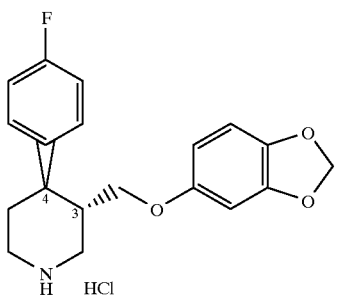

(I)

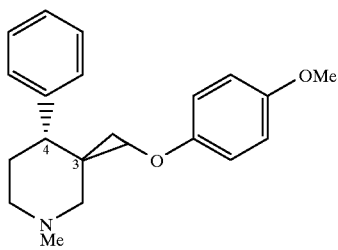

(II)

The stereochemical configurations at the C-3 and C-4 positions of the piperidine ring are critical for the activity of these compounds. For paroxetine, the stereochemistry is 3-S, 4-R and for femoxetine, the stereochemistry is 3-R, 4-S. The method for obtaining the requisite stereochemistry employs the chiral resolution of an intermediate; specifically the menthyl ester hydrobromide salts III and IV as disclosed in U.S. Pat. No. 4,007,196.

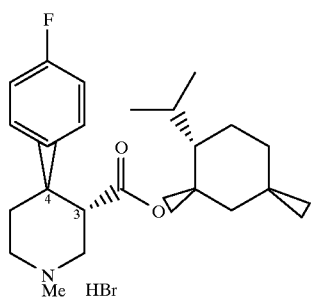

(III)

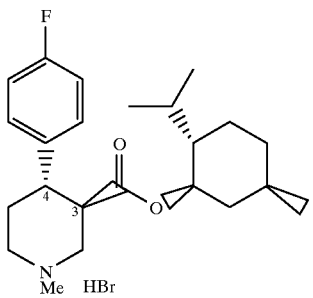

(IV)

Using the previously described synthesis, no control over the stereochemistry at C-4 was obtained. This resulted in the loss of 50% of the material as the wrong diastereomer which represents a severe disadvantage of the above procedure. This motivated us to find a versatile method to control the stereochemistry at C-3 and C-4. It is pertinent to note that recent literature (M. Amat, J. Hidalgo, and J. Bosch, *Tetrahedron Asymmetry*. 7, 1996, pp. 1591–1594) also provides a completely different chiral route to the enantiomer of paroxetine.HCl. The overall yield for this 8-step synthesis is 19.7%.

SUMMARY OF THE INVENTION

We have discovered that by using a starting material of Formula V, wherein R is a selected chiral auxiliary, control of the stereochemistry at the C-3 and C-4 positions of compound V is acquired.

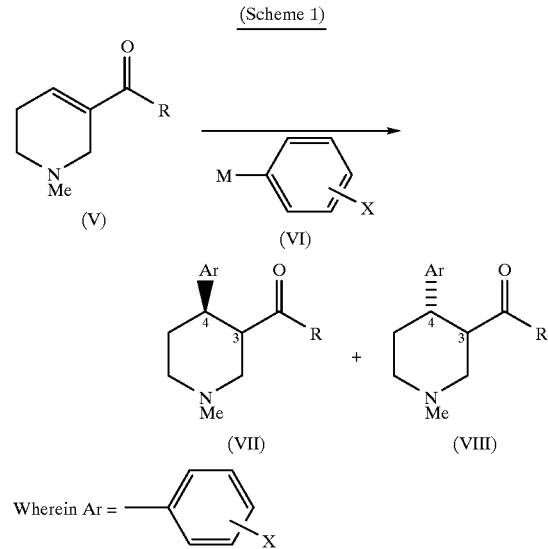

(Scheme 1)

More specifically, according to one aspect of this invention, by the proper selection of R, the 1,4-conjugate addition reaction between various organometallic reagents (VI), the most common of which are where M is a lithium, cuprate, or Grignard (ie., magnesium halides) substituent, for instance, 4-fluorophenylmagnesium bromide or phenylmagnesium bromide, and compounds of formula V proceeds with a high degree of stereoinduction at C-4 to furnish the requisite stereochemistry at C-4 (formula VII, Scheme 1 for paroxetine; formula VIII, Scheme 1 for femoxetine).

Effective chiral control groups or auxiliaries are generally substituted menthol-, substituted camphor-, carbohydrate-, amino acid-, substituted and unsubstituted ephedrine-, substituted and unsubstituted binaphthyl-, chiral diol-, and substituted oxazolidinone-based. We have found that particularly effective chiral control groups are derivatives of menthol (Examples 1, 2, and 3 in Table I) and camphor (Example 4 in Table I). Other examples of effective chiral control groups, R, include 10-dicyclohexylsulfamoyl-isoborneoxy-, 8-naphthylmenthoxy-, the anion of 4-benzyl-2-oxazolidinone, and 1,2:5,6-di-O-isopropylidene-3-oxy-glucose. For a more comprehensive review of chiral control groups, see the article by Rossiter and Swingle, Chem. Rev., 92, 1992, pp. 771–806. Examples of the organometallic reagent of formula VI are where X is hydrogen, alkyl having 1–4 carbon atoms, $C_{1-6}$ alkoxy, trifluoro $C_{1-6}$ alkyl, hydroxy, phenyl $C_{1-6}$ alkyl, methylthio, or halogen most preferably fluoro or hydrogen; and M is a lithium, cuprate, or Grignard, most preferably a Grignard. Examples of Ar, wherein Ar is a group of formula IX,

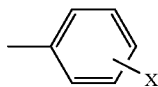

(IX)

are where X is hydrogen, alkyl having 1–4 carbon atoms, $C_{1-6}$ alkoxy, trifluoro $C_{1-6}$ alkyl, hydroxy, phenyl $C_{1-6}$ alkoxy, methylthio, or halogen, most preferably fluoro of hydrogen.

The reaction maybe performed in an organic solvent which favours 1,4-addition over 1,2-addition. Suitable solvents include hydrocarbons (aliphatic and aromatic) and halogenated hydrocarbons. Particularly suitable solvents that can be used include benzene, toluene, tetrahydrofuran, t-butyl methyl ether and diethyl ether. Preferable solvents are toluene and diethyl ether. In general, 1.4–2.0 equivalents of the organometallic reagent are used for every 1.0 equivalent of reactant of formula V. The reaction is preferably carried out under an inert atmosphere, for example under argon or nitrogen. The reaction is conducted at reduced temperature, preferably the reaction temperature is maintained at or below 0° C. Most preferably the reaction temperature is maintained at −5° C. to −15° C. Under these conditions, the reaction is complete in less than 2 hours.

The relative amounts of stereoinduction at C-4 produced by the processes according to another aspect of the invention are tabulated in Table I for various R groups wherein R is selected from Examples 1–4. Other suitable chiral auxiliaries include other substituted menthol-based auxiliaries such as 8-naphthylmenthoxy, other substituted camphor-based auxiliaries such as 10-dicyclohexylsulfamoyl-isoborneoxy, and substituted and unsubstituted ephedrine-, carbohydrate-, amino acid-, substituted and unsubstituted binapthyl-, chiral diol-, and substituted oxazolidinone-based chiral auxiliaries. This list is representative of chiral auxiliaries, and is not to be interpreted in a limiting sense.

TABLE I

| Example No. | R | (VII) | (VIII) |
|---|---|---|---|
| 1. | Ph-menthyl (with methyl wedge) | 3.7 | 1.0 |
| 2. | Ph-cyclohexyl derivative | 4.0 | 1.0 |
| 3. | Ph-cyclohexyl derivative (epimer) | 1.0 | 4.0 |

TABLE I-continued

| | Ar O<br>structure (VII) | Ar O<br>structure (VIII) |
|---|---|---|
| Example No. R | | |
| 4. (camphorsulfonamide group) | 1.0 | 0 |

It should be noted that any process yielding a ratio greater than one to one is an improvement over the prior art. Also of particular note is the total control of the stereochemistry at C-4 by judicious choice of R as illustrated in examples 2 and 3, Table I. Those processes producing the greater ratio of VII over VIII in the case of paroxetine, and VIII over VII in the case of femoxetine are the most useful with Examples 1–4 being most preferred. The starting formula V may be conveniently prepared according to the procedures outlined in literature such as Organic Synthesis, Vol VIII, 1993, pp. 350–353 or J. Org. Chem., 60, 1995, pp. 2271–2273.

Another aspect of this invention is that the stereochemistry at C-4 can then be used to induce the correct stereochemistry at C-3 using procedures such as epimerization. Thus, when the addition products VII and VIII (Scheme 2) are contacted with a suitable strong base such as potassium tert-butoxide or sodium methoxide, the thermodynamically more stable C-3, C-4-trans relative stereochemistry is obtained. Further elaboration, as depicted in Scheme 2, provides paroxetine (I) and femoxetine (II). Other processes for controlling the stereochemistry at C-3 based on the stereochemistry at C-4 are described in U.S. Pat. Nos. 4,007,196, 5,039,803, Acta Chemica Scandinavica, 1996, 50: pp. 164–9 and Tetrahedron Letters, 1983, Vol. 24, No. 46, 99, 5151–5152. Further elaboration as depicted in Scheme 3 provides paroxetine (I) and femoxetine (II).

According to another aspect of this invention, the process may comprise of the steps outlined in Scheme 2 to prepare paroxetine from the pivotal intermediate VII or likewise, femoxetine from VIII.

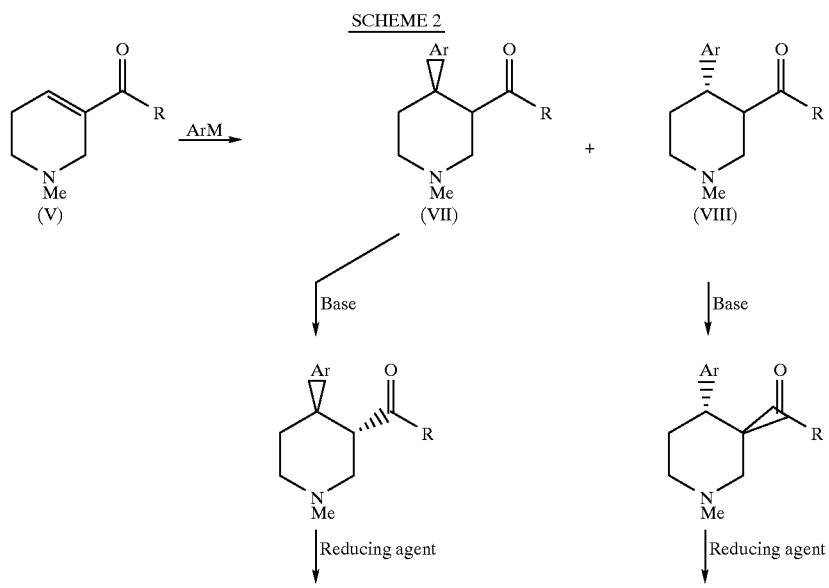

SCHEME 2

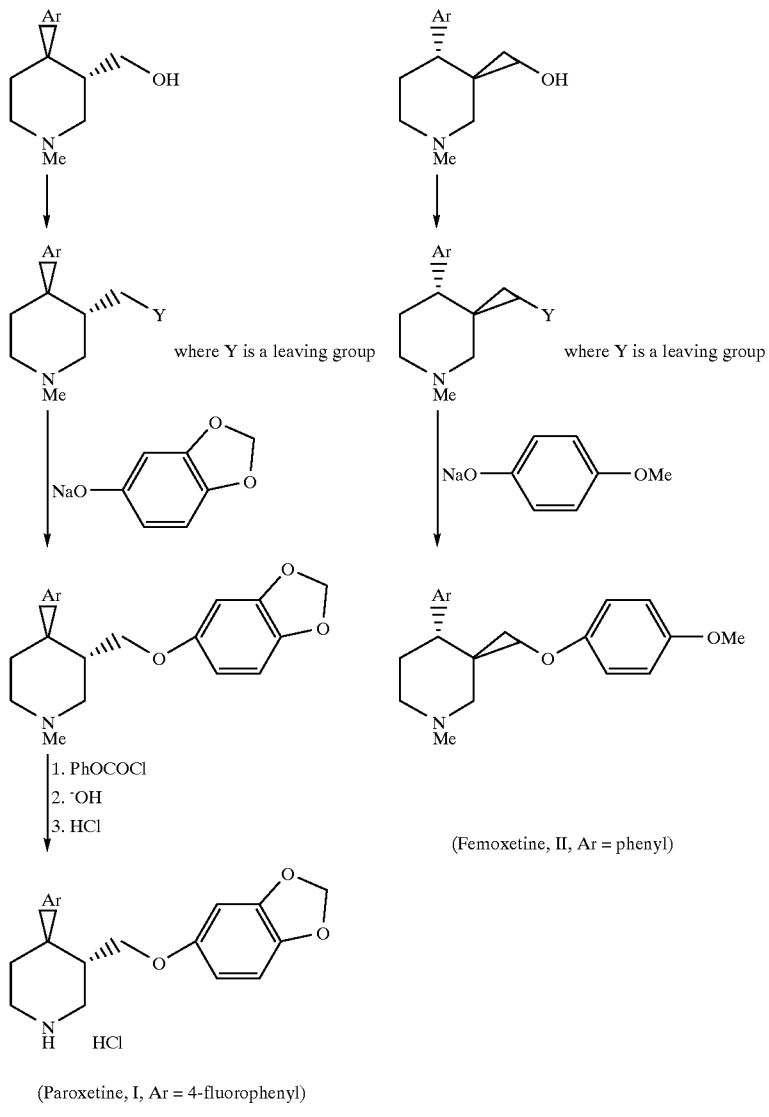
(Femoxetine, II, Ar = phenyl)
(Paroxetine, I, Ar = 4-fluorophenyl)
where Ar is 4-fluorophenyl or phenyl.
According to another aspect of this invention, the process may comprise of the known steps outlined in Scheme 3 to prepare paroxetine from X or femoxetine from intermediate XI.
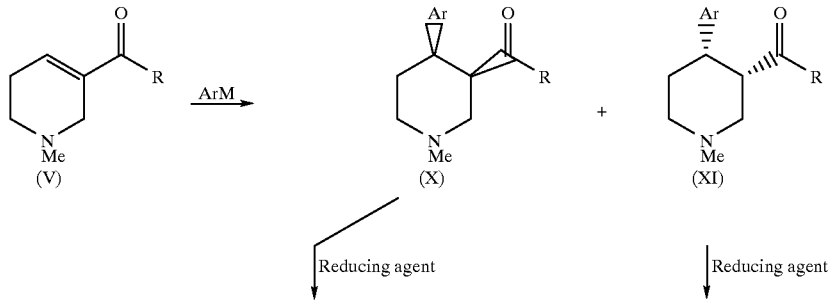

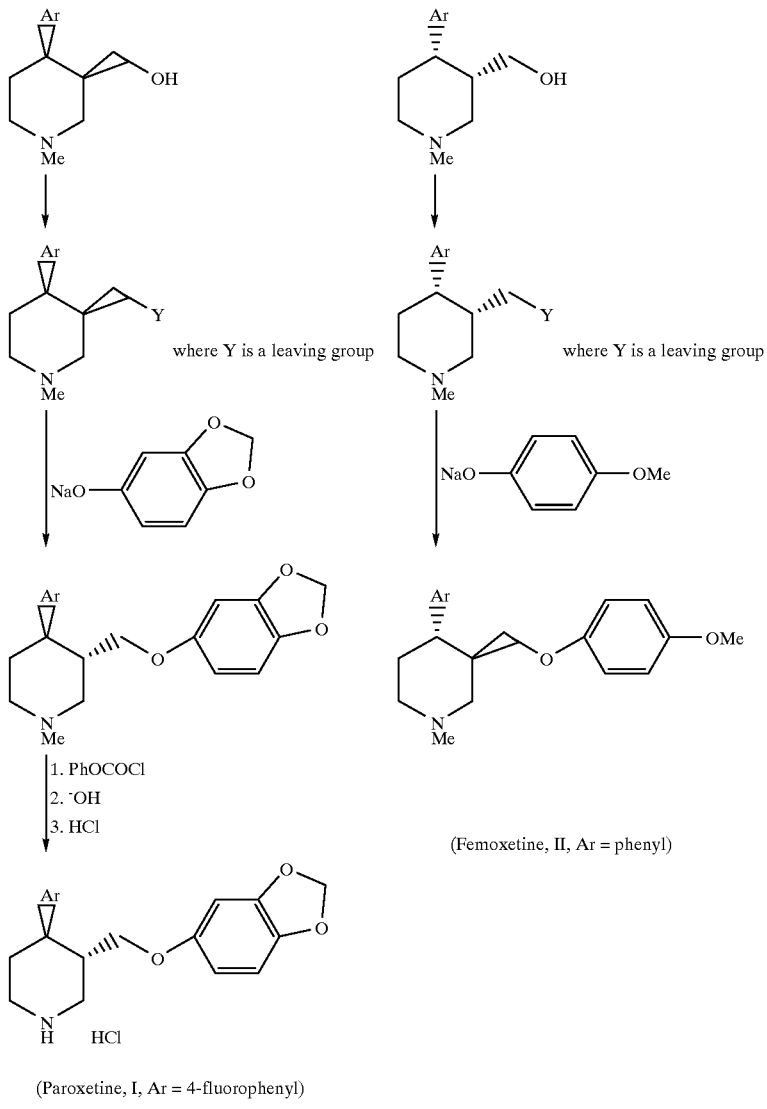

(Paroxetine, I, Ar = 4-fluorophenyl)

where Ar is 4-fluorophenyl or phenyl.

The following examples are illustrative of the invention and are not to be construed as limiting the scope of the invention in any manner.

A. General procedure for the preparation of compounds of formula V having menthol-based auxiliaries is set out below (Example numbers 1–3, Table I).

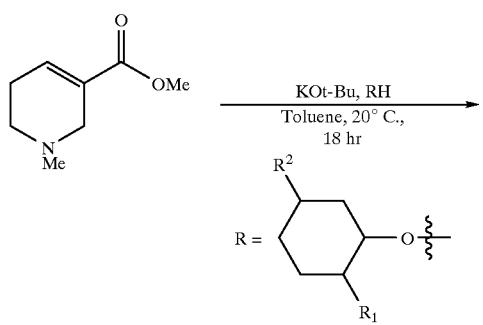

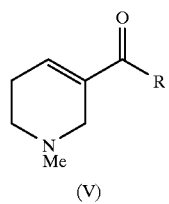

wherein R is as defined

EXAMPLE 1

Procedure for R=8-phenylmenthoxy (No. 1, Table I):

To a round bottom flask was added (–)-(1R,2S,5R)-8-phenylmenthol (2.43 g, 10.5 mmol) and toluene (40 mL). A portion of the toluene was removed using the rotoevaporator and to this solution was added potassium tert-butoxide (1.52 g, 13.6 mmol, 1.3 eq) and the solution was stirred for 15 minutes at which point arecoline was added (2.11 g, 13.6 mmol, 1.3 eq). Stirring was continued 20 hours and saturated aqueous sodium chloride was added and the mixture stirred a further 5 minutes. The aqueous and organic layers were separated and the aqueous layer was back-extracted with toluene. The combined organic layers were washed with brine, filtered through a pad of Celite™, and the volatiles removed using the rotoevaporator. The material was further purified by silica gel flash chromatography (ethyl acetate) to provide the desired (1R,2S,5R)-8-phenylmenthyl ester of arecoline as a pale-yellow, viscous oil (2.97 g, 80% yield.

The above procedure was also used to prepare the, -unsaturated esters required for Examples numbers 2 and 3 in Table I.

B. General procedure for Grignard reaction on compounds having menthol-based auxiliaries and the subsequent epimerization (Numbers 1–3, Table I)

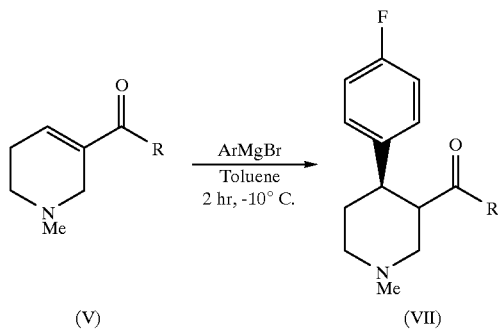

wherein R and Ar are as defined

EXAMPLE 2

Procedure for R=(−)-8-phenylmenthoxy and Ar is 4-fluorophenyl (No. 3, Table I):

To a round bottom flask was added the (1R,2S,5R)-8-phenylmenthyl ester of arecoline (compound of Example 1) (2.93 g, 8.25 mmol) and toluene (90 mL). A portion of the toluene was removed using a rotoevaporator. The mixture was cooled to −10° C. under a nitrogen atmosphere and, with stirring, 4-fluorophenylmagnesium bromide (2M in diethylether) (8.25 mL, 16.5 mmol, 2.0 eq) was added dropwise. After a further 1 hour at this temperature, the reaction was quenched using saturated aqueous ammonium chloride (20 mL) (Exotherm). The organic and aqueous layers were separated and the aqueous layer was back-extracted with toluene. The combined organic layers were washed with brine, filtered through a pad of Celite™ and the volatiles removed under reduced pressure. This afforded a quantitative crude yield (3.7 g) of the 1,4-adduct as a viscous, yellow oil and having 79% of the R configuration and 21% of the S configuration at C-4.

The above procedure was also used to prepare the 1,4-Grignard adducts for Example numbers 2 and 3 in Table I.

EXAMPLE 3

Procedure for Epimerization:

The material from Example 2 above was further processed by epimerization to the trans-C-3, C-4-diastereomers by contact with potassium tert-butoxide (1.5 eq) in toluene (5 vol). This provided a 90% combined yield of the (3S,4R)- and (3R,4S)-diastereomers which were readily separated by silica gel preparative thick layer chromatography (25% acetone in chloroform) to give a 3.7:1 ratio (by weight) between the major (3S,4R)- and minor (3R,4S)-diastereomers. $^{13}$C NMR of the (3S,4R)-diastereomer (CDCl$_3$): 21.60. 24.34, 26.94, 28.39, 31.06, 32.97, 34.37, 39.72, 41.19, 42.57, 46.01, 49.83, 49.97, 55.60, 58.04, 75.12, 114.83, 115.11, 125.16, 125.48, 127.87, 129.08, 129.18, 139.46, 150.75, 159.88, 163.12, 172.06 ppm. Mass spectral data: Direct electron impact of the (3S, R)-diastereomer=13.8% (M$^+$), 100% (M$^+$−215). High resolution mass=451.2871 amu (451.2890 theoretical). $^{13}$C NMR (CDCl$_3$): 21.45, 26.54, 26.69, 30.87, 33.48, 34.26, 39.83, 40.72, 45.22, 46.12, 48.90, 49.83, 55.67, 57.17, 74.34, 114.82, 115.10, 125.26, 125.43, 127.85, 129.18, 129.28, 138.61, 151.21, 159.98, 163.56, 172.69 ppm. Of the (3R,4S)-diastereomer, direct electron impact=13.3% (M$^+$), 100% (M$^+$−215). High resolution mass=451.2872 amu (451.2890 theoretical).

The above procedure was also used to prepare the epimerized products from Example numbers 2 and 3 in Table I.

C. General procedure for Cuprate reaction on compounds having menthol based auxiliaries. (Examples 1–3, Table I)

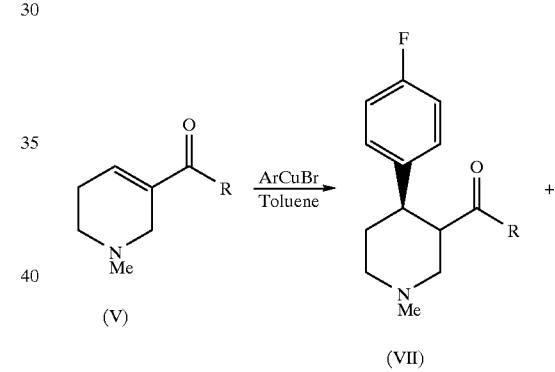

wherein R and Ar are as defined

EXAMPLE 4

Procedure for R=(1R,2S)-trans-cumenecyclohexyloxy and Ar is 4-fluorophenyl (No. 2, Table I):

To an oven dried flask and cooled under nitrogen was added copper (I) bromide-dimethyl sulfide complex (1.20 g, 5.8 mmol, 2.0 eq) in toluene (10 mL) and the reaction mixture cooled to −70 to −78° C. To this suspension was added 4-fluorophenylmagnesium bromide (2.0 M in diethyl ether) and the mixture stirred. To this mixture was added the (1R,2S)-trans-cumenecyclohexyl ester of arecoline (1.00 g, 2.93 mmol) in toluene (10 mL). The mixture quickly became homogeneous and after 30 minutes, was warmed to −10° C., and kept at this temperature for 16 hours whereupon it was quenched with saturated aqueous ammonium chloride (Exotherm). The mixture was warmed to 20° C. and water and toluene were added. The solution was transferred to a separatory funnel and the layers separated. The aqueous layer was back-extracted with toluene and the combined organic layers were washed with brine (2×10 mL) and filtered through a Celite™ pad. The volatiles were removed under reduced pressure to afford a quantitative crude yield of the 1,4-adduct as a pale-green, viscous oil and having 80% of the R configuration and 20% of the S configuration at C-4.

EXAMPLE 5

Procedure for Epimerization:

The material from Example 4 was further processed by epimerization to the trans-C-3, C-4 diastereomers using the identical procedure as described in Example 3. This provided a 94% combined yield of the (3S,4R)- and (3R,4S)-diastereomers in a 4:1 ratio.

D. Procedure for preparation of compounds of formula V having camphor-based auxiliaries (Example 4, Table I).

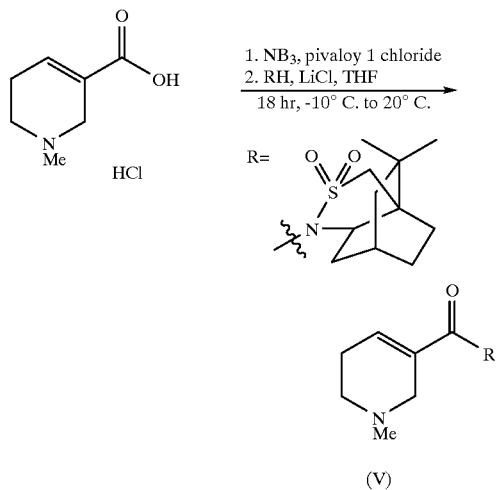

wherein R is as defined

EXAMPLE 6

Procedure for R=(2,10)-camphorsultamyl (No. 4, Table I):

In an oven dried, round bottom flask equipped with a nitrogen inlet/outlet line and a magnetic stir bar, was added arecaidine hydrochloride (5.00 g, 22.5 mmol) and tetrahydrofuran (150 mL, distilled from sodium). The solution was cooled to 0 to −5° C. and triethylamine (6.83 g, 67.5 mmol, 3 eq) and pivaloyl chloride (2.44 g, 20.3 mmol) were added. This mixture was stirred at −5 to −10° C. for 2 hours whereupon lithium chloride (1.24 g, 29.3 mmol, 1.3 eq) followed by (1S)-(−)-2,10-camphorsultam (4.26 g, 20.3 mmol, 0.9 eq) were added. The mixture was stirred and then permitted to warm to ambient temperature (20° C.). After stirring a further 16 hours at this temperature, the volatiles were removed using the rotoevaporator. Ethyl acetate (100 mL) and saturated aqueous sodium bicarbonate (50 mL) were added. This mixture was transferred to a separatory funnel and mixed. The organic layer was back-extracted with ethyl acetate and the combined organic layers were washed with brine. The organic layer was dried over sodium sulfate, filtered and the volatiles removed under reduced pressure. The residual material (6.0 g) was precipitated from warm ethyl acetate using hexanes. This provided 3.89 g (57% yield) of the crystalline N-enoyl sultam IV wherein R was the camphor sultam moiety. $^{13}$C NMR (CDCl$_3$): 19.69, 21.08, 25.82, 26.31, 32.94, 37.99, 44.98, 45.24, 47.47, 47.69, 50.46, 52.57, 53.33, 65.09, 131.71, 137.83, 169.19 ppm. Mass spectral data: Direct electron impact: 11.5% (M$^+$+1); Direct chemical ionization: 100% (M$^+$+1). High resolution mass=339.1735 amu (339.1744 theoretical).

E. General procedure for Grignard reaction on compounds having camphor-based auxiliaries (No. 4, Table I).

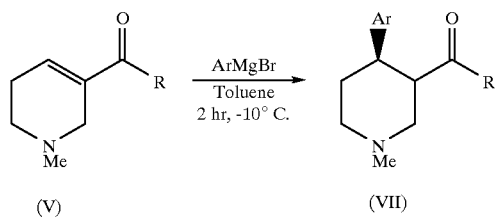

wherein R and Ar are as defined

EXAMPLE 7

Procedure for R=(2,10)-camphorsultamyl and Ar is 4-fluorophenyl (No. 4, Table I):

In a round bottom flask was added the N-enoyl camphor sultam compound IV of Example 6 (R=(1S)-(−)-camphorsultam) (3.65 g, 10.8 mmol) and toluene (110 mL). A portion of the toluene was removed using a rotoevaporator and the reaction mixture was cooled to 0 to −5° C. under nitrogen. The 4-fluorophenylmagnesium bromide (2M in diethyl ether) (8.65 mL, 17.3 mmol, 1.6 eq) solution was added dropwise with stirring over a 20 minute period while maintaining the temperature between 0 to −5° C. After a further 2 hours at this temperature, the reaction mixture was quenched using saturated aqueous ammonium chloride (Exotherm). The organic and aqueous layers were separated. The organic layer was washed with brine, filtered through a pad of Celite™ and the volatiles removed under reduced pressure. This afforded a crude solid which was further purified by silica gel chromatography (EtOAc) to provide 3.0 g (64% yield) of the cis-(3R,4R)-adduct. No other diastereomers were formed (300 MHz Hnmr and TLC). Mass spectral data: Direct electron impact: 15.8% (M$^+$+1); Direct chemical ionization: 100% (M$^+$+1). High resolution mass=435.2112 amu (435.2119 theoretical).

As many changes can be made to the embodiments without departing from the scope of the invention, it is intended that all material be interpreted as illustrative of the invention and not in a limiting sense.

We claim:

1. A process for the preparation of a compound of formula VII:

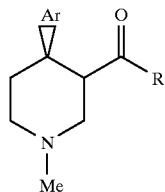

(VII)

wherein Ar is a group of formula IX,

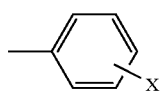

(IX)

in which X is hydrogen, alkyl having 1–4 carbon atoms, $C_{1-6}$ alkoxy, trifluoro $C_{1-6}$ alkyl, hydroxy, methylthio, or halogen and R is a chiral auxiliary selected from substituted menthol-, substituted camphor-, substituted and unsubstituted ephedrine-, carbohydrate-, amino acid-, substituted and unsubstituted binapthyl-, chiral diol-, and substituted oxazolidinone-based auxiliaries which process comprises contacting a compound of formula V:

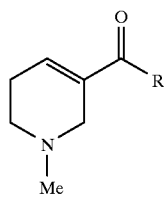

(V)

wherein R is as defined above, with an organometallic of formula VI:

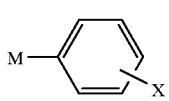

(VI)

wherein X is as defined above, and M is a lithium, cuprate, or Grignard substituent.

2. A process for the preparation of a compound of formula VIII:

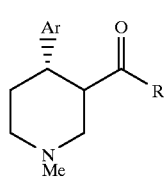

(VIII)

wherein Ar is a group of formula IX,

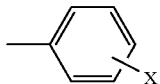

(IX)

in which X is hydrogen, alkyl having 1–4 carbon atoms, $C_{1-6}$ alkoxy, trifluoro $C_{1-6}$ alkyl, hydroxy, methylthio, or halogen and R is a chiral auxiliary selected from substituted menthol-, substituted camphor-, substituted and unsubstituted ephedrine-, carbohydrate-, amino acid-, substituted and unsubstituted binapthyl-, chiral diol-, and substituted oxazolidinone-based auxiliaries which process comprises contacting a compound of formula V:

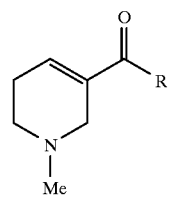

(V)

wherein R is as defined above, with an organometallic of formula VI.

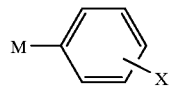

(VI)

wherein X is as defined above, and M is a lithium, cuprate, or Grignard substituent.

3. The process for controlling the stereochemistry at C-3 and C-4 of piperidine compounds of claims 1 or 2 by the 1,4-addition of aryl Grignards to the corresponding chiral 3,4-unsaturated-3-piperidine esters.

4. The process for controlling the stereochemistry at C-3 and C-4 of piperidine compounds of claims 1 or 2 by the 1,4-addition of aryl Grignards to the corresponding chiral 3,4-unsaturated-3-piperidine amides.

5. The process for controlling the stereochemistry at C-3 and C-4 of piperidine compounds of claims 1 or 2 by the 1,4-addition of aryl Grignards to the corresponding chiral 3,4-unsaturated-3-piperidine N-enoylsultams.

6. Process for the synthesis of paroxetine according to the following Scheme:

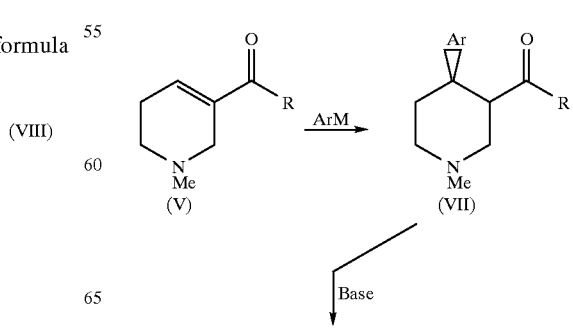

17

-continued

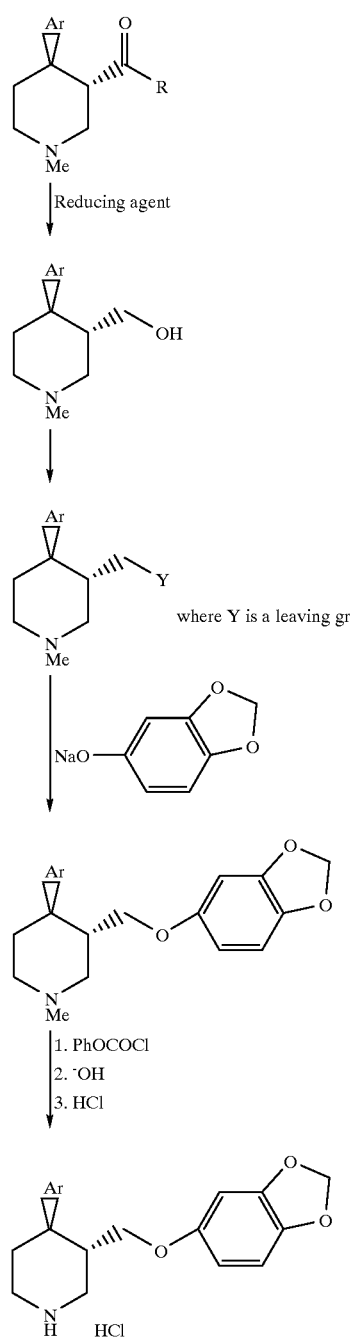

wherein R is a chiral auxiliary selected from substituted menthol-, substituted camphor-, substituted and unsubstituted ephedrine-, carbohydrate-, amino acid-, substituted and unsubstituted binapthyl-, chiral diol-, and substituted oxazolidinone-based auxiliaries, M is a lithium, cuprate or Grignard substituent, and Ar is 4-fluorophenyl.

7. Process for the synthesis of paroxetine according to the following Scheme:

18

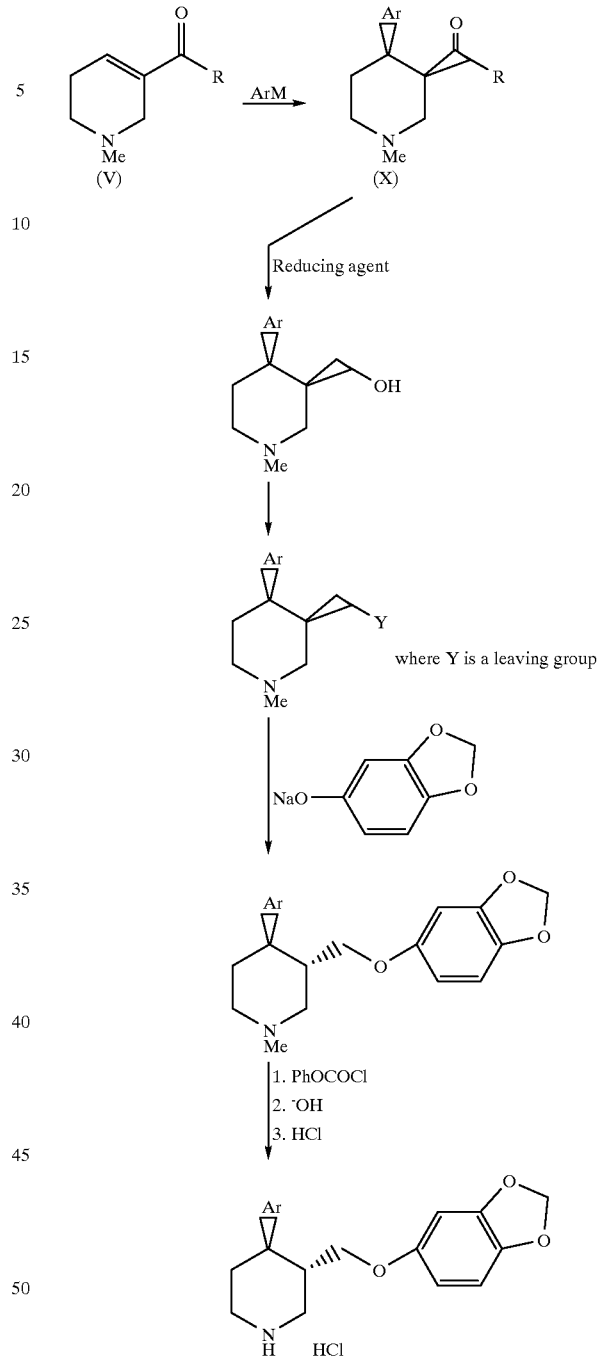

wherein R is a chiral auxiliary selected from substituted menthol-, substituted camphor-, substituted and unsubstituted ephedrine-, carbohydrate-, amino acid-, substituted and unsubstituted binapthyl-, chiral diol-, and substituted oxazolidinone-based auxiliaries, M is a lithium, cuprate, or Grignard substituent, and Ar is 4-fluorophenyl.

8. Process for the synthesis of femoxetine according to the following Scheme:

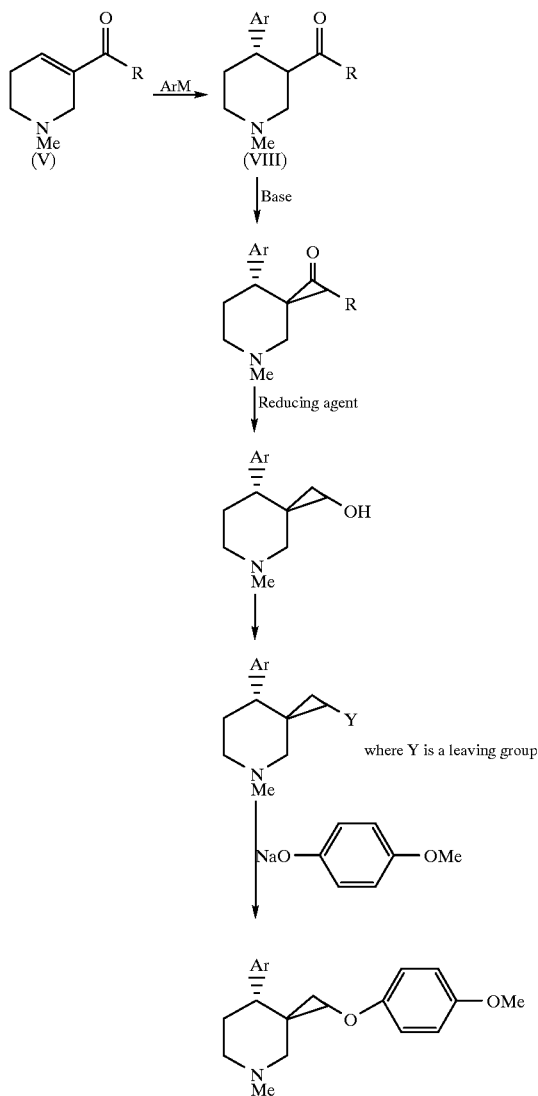

wherein R is a chiral auxiliary selected from substituted menthol-, substituted camphor-, substituted and unsubstituted ephedrine-, carbohydrate-, amino acid-, substituted and unsubstituted binapthyl-, chiral diol-, and substituted oxazolidinone-based auxiliaries, M is a lithium, cuprate or Grignard substituent, and Ar is phenyl.

9. Process for the synthesis of femoxetine according to the following Scheme:

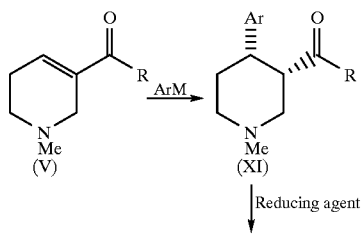

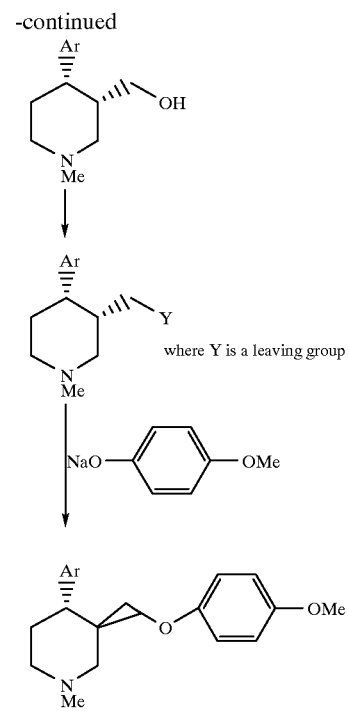

wherein R is a chiral auxiliary selected from substituted menthol-, substituted camphor-, substituted and unsubstituted ephedrine-, carbohydrate-, amino acid-, substituted and unsubstituted binapthyl-, chiral diol-, and substituted oxazolidinone-based auxiliaries, M is a lithium, cuprate or Grignard substituent, and Ar is phenyl.

10. Process of claim 1 wherein R is (1R, 2S,5R)-(−)-8-phenylmenthoxy, Ar is 4-fluorophenyl, and M is a Grignard (ie., magnesium halide).

11. Process of claim 1 wherein R is (1R,2S)-trans-cumenecyclohexyloxy, Ar is 4-fluorophenyl, and M is a Grignard (ie., magnesium halide).

12. Process of claim 1 wherein R is (1S)-(−)-2,10-camphorsultamyl, Ar is 4-fluorophenyl, and M is a Grignard (ie., magnesium halide).

13. Process of claim 1 wherein R is (1R,2S)-trans-cumenecyclohexyloxy, Ar is 4-fluorophenyl, and M is a cuprate.

14. Process of claim 2 wherein R is (1S,2R,5S)-(+)-8-phenylmenthoxy, Ar is phenyl, and M is a Grignard (ie., magnesium halide).

15. Process of claim 2 wherein R is (1S,2R)-trans-cumenecyclohexyloxy, Ar is phenyl, and M is a Grignard (ie., magnesium halide).

16. Process of claim 2 wherein R is (1R)-(+)-2,10-camphorsultamyl, Ar is phenyl, and M is a Grignard (ie., magnesium halide).

17. Process of claim 6 wherein R is (1R,2S,5R)-(−)-8-phenylmenthoxy, Ar is 4-fluorophenyl, and M is a Grignard (ie., magnesium halide).

18. Process of claim 6 wherein R is (1R,2S)-trans-cumenecyclohexyloxy, Ar is 4-fluorophenyl, and M is a Grignard (ie., magnesium halide).

19. Process of claim 7 wherein R is (1S)-(−)-2,10-camphorsultamyl, Ar is 4-fluorophenyl, and M is a Grignard (ie., magnesium halide).

20. Process of claim 6 wherein R is (1R,2S)-trans-cumenecyclohexyloxy, Ar is 4-fluorophenyl, and M is a cuprate.

21. Process of claim 8 wherein R is (1S,2R,5S)-(+)-8-phenylmenthoxy, Ar is phenyl and M is a Grignard (ie., magnesium halide).

22. Process of claim 8 wherein R is (1S,2R)-trans-cumenecyclohexyloxy, Ar is phenyl, and M is a Grignard (ie., magnesium halide).

23. Process of claim 9 wherein R is (1R)-(+)-2,10-camphorsultamyl, Ar is phenyl, and M is a Grignard (ie., magnesium halide).

* * * * *